United States Patent [19]

Klapper

[11] Patent Number: 4,676,746
[45] Date of Patent: Jun. 30, 1987

[54] ADJUSTABLE ORTHODONTIC BRACKET ASSEMBLY

[76] Inventor: Lewis Klapper, 744 Falls Cir., Lake Forest, Ill. 60045

[21] Appl. No.: 870,315

[22] Filed: Jun. 3, 1986

[51] Int. Cl.⁴ ............................................. A61C 7/00
[52] U.S. Cl. ..................................................... 433/16
[58] Field of Search .............................. 433/16, 9, 6, 8

[56] References Cited

U.S. PATENT DOCUMENTS

| | | | |
|---|---|---|---|
| 3,421,221 | 1/1969 | Silverman et al. | 433/6 |
| 3,721,005 | 3/1973 | Cohen | 433/16 |
| 4,243,386 | 1/1981 | Kawaguchi | 433/9 |

Primary Examiner—Robert Peshock
Attorney, Agent, or Firm—Robert A. Brown

[57] ABSTRACT

An adjustable orthodontic bracket assembly that avoids the need to twist and bend arch wire to correct the position of a malposed tooth. The assembly includes a base member attached directly to a tooth, a bracket holder and interfitting means for engagement with the base member which is adjustable relative to the longitudinal axis of the arch wire, and passive fastening means that connects the assembly together without creating frictional forces that could cause disassembly of the component parts. The mechanism is adaptable to control separately vertical, angular and torque adjustments of a tooth by the use of cooperative, interchangeable, adjustable, component parts within the assembly.

16 Claims, 28 Drawing Figures

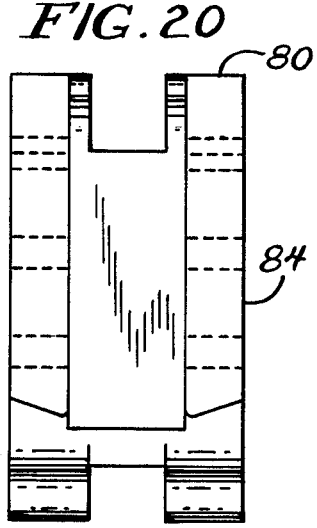
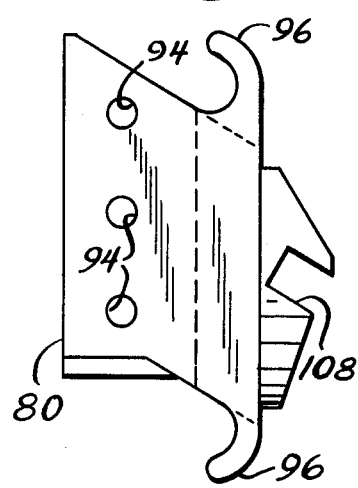
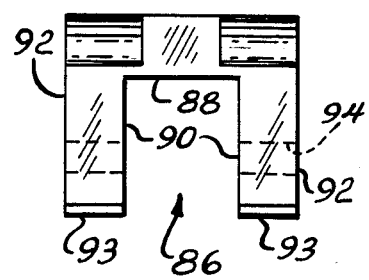
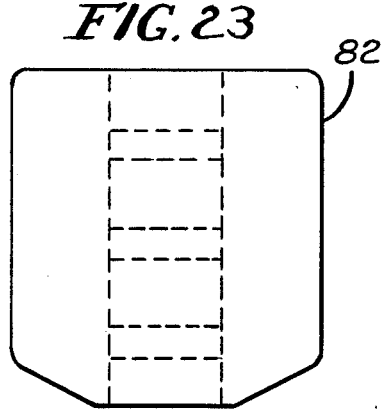
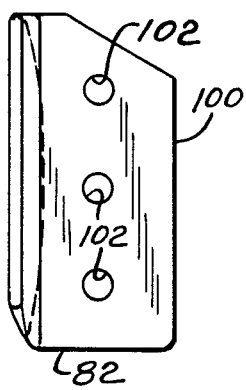
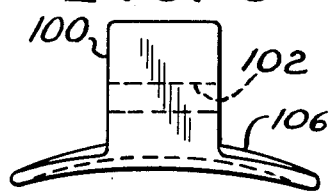
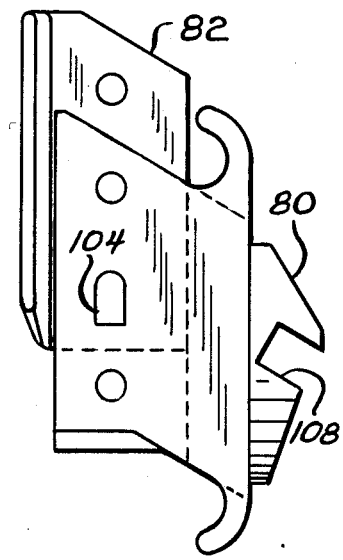
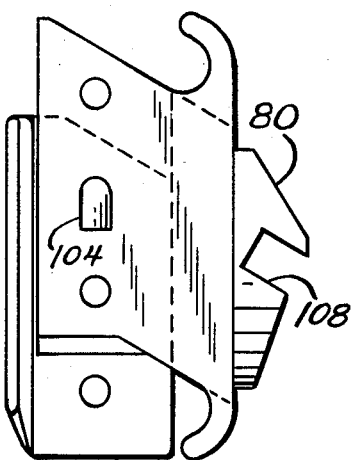

ADJUSTABLE ORTHODONTIC BRACKET ASSEMBLY

BACKGROUND OF THE INVENTION

The present invention relates generally to orthodontic appliances and more particularly to orthodontic brackets that provide for vertical and angular adjustment, can be unrestrictively interchanged and include passive fastening means for locking the brackets securely in a desired position.

The practice of orthodontics requires the application of appliances to teeth so that they can be adjusted into proper vertical and horizontal alignment along both the upper and lower jaws of the mouth. The usual procedure has been to apply an individual metal band around each tooth, secure as by spot welding a bracket to each metal band and anchor to each bracket a continuous arch wire that would bind together all of the teeth to be straightened in the lower or upper jaw. In order to make desired adjustments to a respective tooth, it was necessary to bend or twist the arch wire in one or more directions such as vertically, inwardly or outwardly so as to retract a tooth into correct occlusion. Bending the wire is intended to accomplish proper positioning of a tooth by vertical upward or downward movement, forward or backward tipping movement and torque adjustment by rotative movement relative to the longitudinal axis of the arch wire.

In attempting to correct the position of each tooth, it is usually necessary to make a number of changes in bends or twists of the arch wire. Each bend or twist is accomplished while the wire is disengaged from respective brackets on adjoining teeth. After the bend is made and the wire is reengaged in the adjacent brackets, rotation of the wire in slots of the brackets results in undesirable tooth movement effects. In addition, each corrective bend would likely cause a reaction force in the wire secured to an adjoining or nearby tooth which in turn would require additional bending or twisting of the arch wire to obtain the desired result. Consequently, it would be difficult to achieve an absolutely correct positioning of each and every tooth in the jaw.

Various attempts to solve the problems of the prior art have been made, such as providing an anchor member welded to the metal band that surrounds the tooth and including a removable socket or channel member that has a slot for receiving the arch wire. A multitude of sockets are required, each having a different orientation of its wire receiving slot, ranging from various horizontal positions between the upper and lower extremities of the socket to any number of slot positions angled downwardly from the horizontal to an almost vertical position. This concept is disclosed in Stifter, U.S. Pat. No. 2,908,974.

In Prins U.S. Pat. No. 4,243,387 an adjustable bracket is disclosed that comprises a base member for securement to a tooth, a force receiving member and retaining means in the form of a screw. The base member and the force receiving member have respectively a concave surface and a convex surface that join together in complementary relationship and are fixed together by the screw. The force receiving member is adaptable for spherical movement on the base and is secured in a desired position by the screw. However, a large opening is required in the force receiving member in order to make spherical adjustments and maintain a particular position by intense frictional engagement by the screw.

In Karrakussoglu, U.S. Pat. No. 4,353,692 there is disclosed an orthodontic appliance that includes a complex aggregation of parts including a base member, a slidable member for movement within a recessed way of the base, a holder for receiving a bracket and frictional screw fastening means for pressing the holder and bracket against the base in a desired position. When the appliance of this disclosure is scaled to a size that may be mounted on a tooth, it is readily seen that manufacture of a screw and a threaded hole in the base would be extremely difficult and very expensive to make, if indeed, it is even possible to do so. Further, the pressure required to maintain the screw in a secured position is certain to set up forces that result in stress fractures in the slide that is intended to move along the recessed way of the base. If intense pressure of the screw is not maintained, it will likely loosen during eating and chewing activity by a patient.

SUMMARY OF THE INVENTION

Accordingly, it is a primary object of the present invention to provide an improved adjustable orthodontic bracket assembly that avoids the need to bend or twist orthodontic wire in order to correct the position of a malposed tooth.

It is a further object of the present invention to provide an adjustable orthodontic bracket assembly that separates the control of vertical and angular adJustment to correct the position of a malposed tooth.

An additional object of the present invention is to provide an adjustable bracket assembly that avoids the need for frictional locking means to maintain the assembly in a desired position to change the position of a malposed tooth.

It is still a further object of the present invention to provide an adjustable bracket assembly having interchangeable brackets for control of tip or of angular adjustment of a malposed tooth.

Another object of the present invention is to provide a bracket assembly wherein torque adjustment of a malposed tooth is accomplished by slidable bracket means removably securable to a base member attached to the tooth.

A further additional object of the present invention is to provide a bracket assembly wherein vertical adjustment of a malposed tooth is maintained in a desired position by interlocking means between a base member and a bracket holder.

Another object of the present invention is to provide a bracket assembly wherein a plurality of discrete vertical positive locking adjustments accomplish constant resistance against chewing forces that occur during eating activity by a patient.

An improved adjustable orthodontic bracket assembly in accordance with the present invention comprises base member means having an arcuate surface bondable to a buccal surface of a tooth, or otherwise secured to the tooth by having the base member means welded to an orthodontic band, the base member including vertical track means disposed on a side opposite from the arcuate surface, holding means adaptable to be disposed selectively on the track means of the base in locking engagement therewith, and passive fastening means for maintaining the holding means and the base member in one of a plurality of selective positions theretogether.

BRIEF DESCRIPTION OF THE DRAWINGS

The foregoing and other characteristics, objects, features and advantages of the present invention will become more apparent upon consideration of the following detailed description, having reference to the accompanying figures of the drawings, wherein:

FIG. 20 is a frontal elevational view of a bracket holder comprising an alternate embodiment of the invention.

FIG. 21 is a side elevational view of the bracket holder shown in FIG. 21.

FIG. 22 is a top plan view of the bracket holder shown in FIGS. 20 and 21.

FIG. 23 is a frontal elevational view of a base member comprising an alternate embodiment of the invention.

FIG. 24 is a side elevational view of the base member shown in FIG. 23.

FIG. 25 is a top plan view of the base member shown in FIGS. 23 and 24.

FIG. 26 is a side elevational view of the alternate embodiment bracket assembly showing the holder secured in a middle position to the base member.

FIG. 27 is a side elevational view of the alternate embodiment bracket assembly showing the holder secured to an upper most position on the base member.

FIG. 28 is a side elevational view of the alternate embodiment bracket assembly showing the holder secured to a lower most position on the base member.

DESCRIPTION OF A PREFERRED EMBODIMENT

Figure 1:
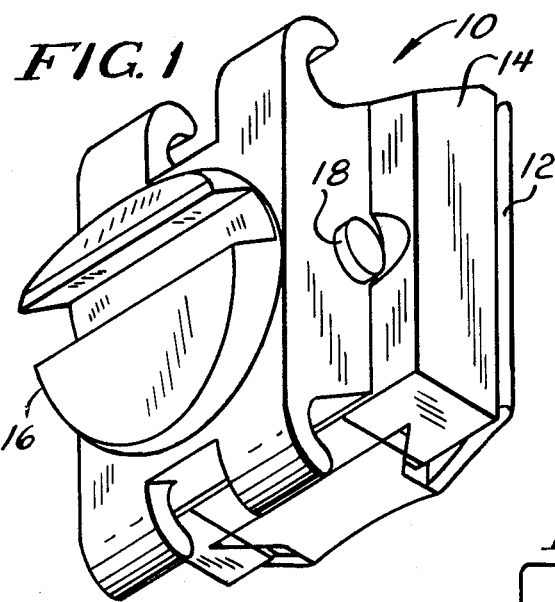
FIG. 1 is a perspective view of an orthodontic bracket assembly including a base, bracket holder and insert.
Figure 2:
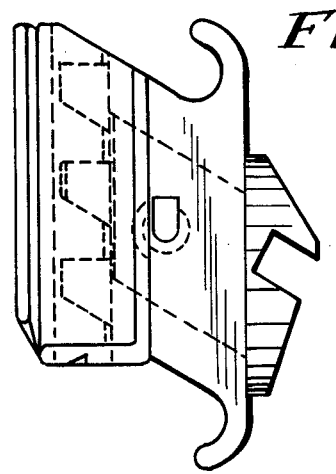
FIG. 2 is a side elevational view of the bracket assembly showing an internal association of the assembled parts and depicting an insert disposed within a bracket holder and in meshed relationship with the track of the base member.
Figure 3:
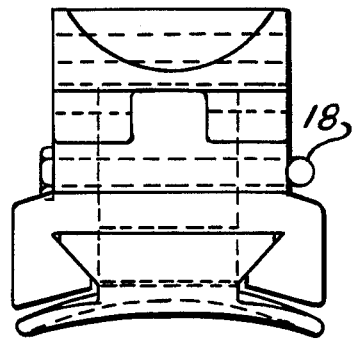
FIG. 3 is a top plan view of the bracket assembly depicting the base, holder, insert and passive fastener assembled together.
Figure 4:
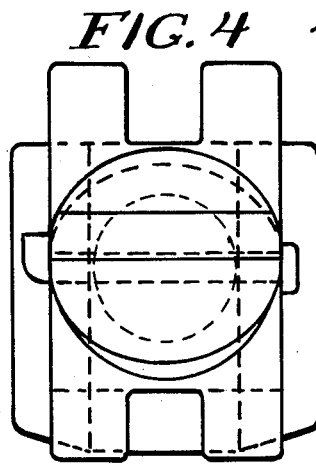
FIG. 4 is a frontal elevational view of the bracket assembly taken along the lines of 4—4 of FIG. 2.

Referring to the several views of the drawing wherein like parts are identified by like reference numerals, a bracket assembly, generally identified by reference numeral 10 comprises a base 12, a bracket holder 14, an insert 16, and a pin 18.

Figure 8:
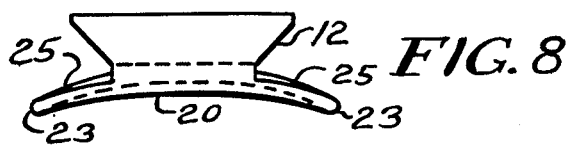
FIG. 8 is a top plan view of the base member of the bracket assembly showing a curved surface that is attached to a tooth.
Figures 9, 10:
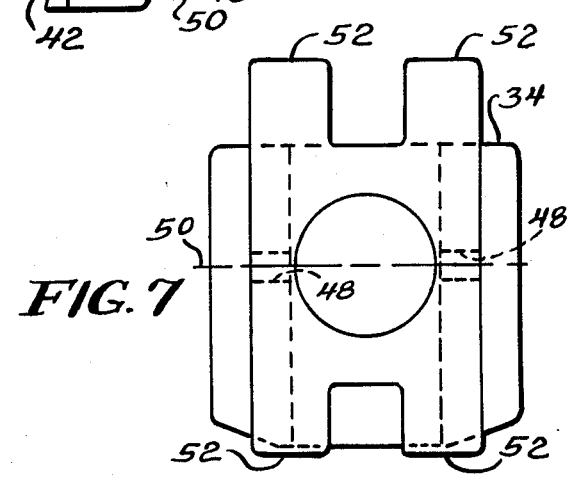
FIG. 9 is a frontal elevational view of the base member of the bracket assembly.
FIG. 10 is a side elevational view of the base member of the bracket assembly showing details of the dove-tailed track section.

With particular reference to FIGS. 8-10, the base 12 comprises a generally arcuate surface 20 adaptable to be bonded, welded or otherwise fixedly secured to a facial or buccal surface of any one of teeth of the mouth including incisors, canines, pre-molars and molars. In the example shown, the base 12 is for attachment to a first molar, a tooth which has a very large angle between its buccal surface and the plane of a flat, rectangular arch wire.

The base 12 includes at its outer or buccal side a series of outwardly extending, cantileverly supported ledge members 22 forming a dove-tailed track 24 having a plurality of notches 26 between the ledge members 22. As best seen in FIG. 10, the notches 26 are delineated by a generally horizontal upper surface 28, a generally downward sloping oblique surface 30 and a substantially vertical surface 32 extending between the surfaces 28 and 30. The dove-tailed track 24 serves as an attachment and guide for the bracket holder 14 which slides vertically thereon, as will be hereinafter described in detail.

Figure 5:
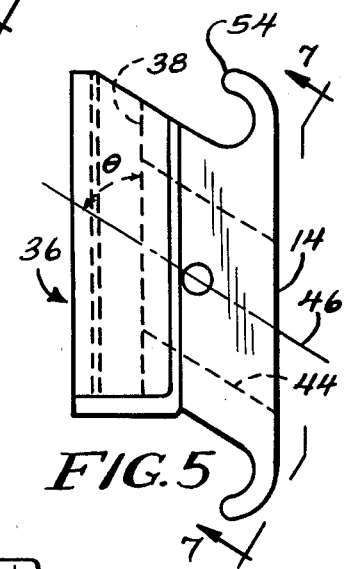
FIG. 5 is a side elevational view of the bracket holder as a single component part.
Figure 6:
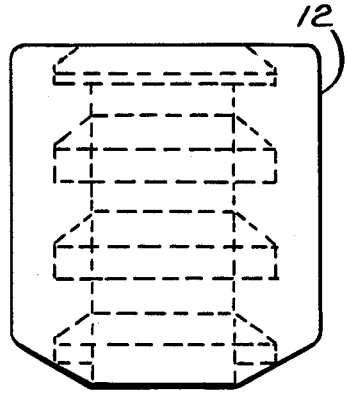
FIG. 6 is a top plan view of the bracket holder.
Figure 7:
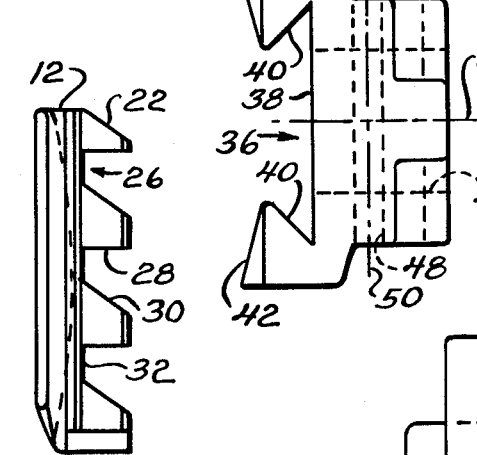
FIG. 7 is a frontal elevational view of the bracket holder taken along lines 7—7 of FIG. 5.

The bracket holder 14, as best seen in FIGS. 5-7 comprises a body member 34 formed generally in the shape of a cube having a substantially vertical slot 36 including surface 38 and two inwardly extending vertical surfaces 40 forming in cross section a generally trapezoidal shape having an open end. Vertical surfaces 42 are disposed outwardly from slot 36 and are shaped to be generally complementary to, adaptable to and abut in assembled relationship with outer surfaces 25 of flanges 23 of base 12. The bracket holder 14 further comprises a cylindrical bore 44 having an axis 46 disposed obliquely from the vertical surface 38 of slot 36 and being generally parallel with the sloping oblique surfaces 30 of the base 12. It will be noted the axis 46 of bore 44 forms an angle $\theta$ with vertical surface 38 of slot 36. This angle is preferably of a different value for each tooth in the mouth and can be manufactured to any desired angle so as to compensate for any differences between the slopes of the surfaces of teeth to which the base is attached.

These angular differences in relationship between the slope of a slot and the vertical side of a base member are termed "built in torque adjustment" and refer to any combination of angular changes in a slot of a holder which permits the placement of flat, untwisted rectangular or other orthodontic wire in a respective slot of each bracket attached to all of the teeth without making adjustments in the wire for each individual tooth slope. This "built in torque adjustment" has been accomplished in one of two ways: the first is merely to form the slot of a bracket member at an angle to the upright side of its member; the second is to modify the curved surface of a base that attaches to a tooth so that the slot forms an angle to the tooth surface (this is considered a more desirable method as it brings all the slots on the variously shaped teeth to the same vertical level as well as compensating for the surface angulations of the teeth). The present invention avoids each of the above two mentioned ways by providing in an insert any of a plurality of different angles of angular inclination of the slot around the longitudinal axis of the arch wire and thereby impart a desired torque action on a tooth. Generally horizontal transverse bores 48 are formed through the body member 34 having a coincidental axis 50 that intersects the longitudinal axis 46 of bore 44 at a point exteriorly outwardly of the slot 36. Body member 34 additionally includes upwardly and downwardly extending projections 52 that terminate at their outer ends in hook-like members termed tie wings. It should be noted that the projections 52 and tie wings 54 are an integral part of the bracket holder 14 and provide means to permit ligation of the orthodontic wire in a known manner to the bracket holder 14.

Figure 11:
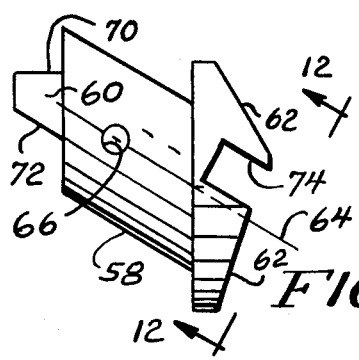
FIG. 11 is a side elevational view of the insert as a single component part.
Figure 12:
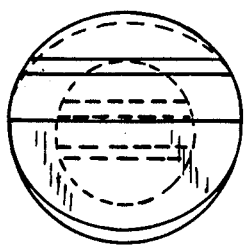
FIG. 12 is a frontal elevational view of the insert taken along the lines 12—12 of FIG. 11.
Figure 14:
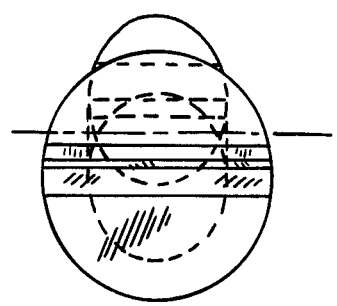
FIG. 14 is a frontal elevational view of the insert as seen from the right side of FIG. 11.
Figure 13:
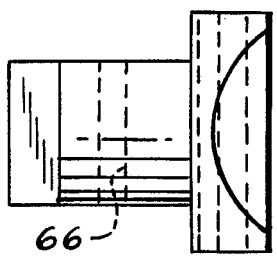
FIG. 13 is a top plan view of an insert that forms a part of the bracket assembly.
Figure 15:
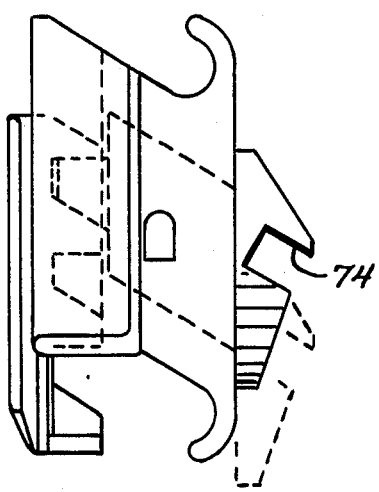
FIG. 15 is a side elevational view of the bracket assembly showing in dotted lines an insert secured in an upper most notch of a base member.
Figure 16:
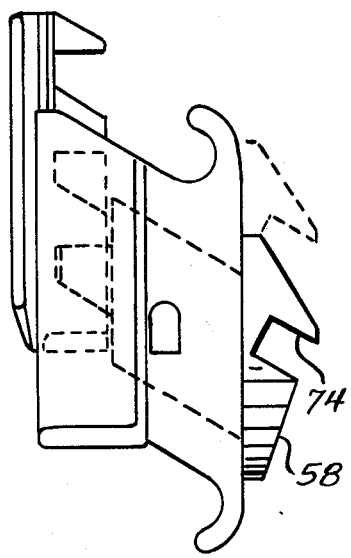
FIG. 16 is a side elevational view of the bracket assembly showing in dotted lines an insert secured in a lower most notch of a base member.
Figure 17:
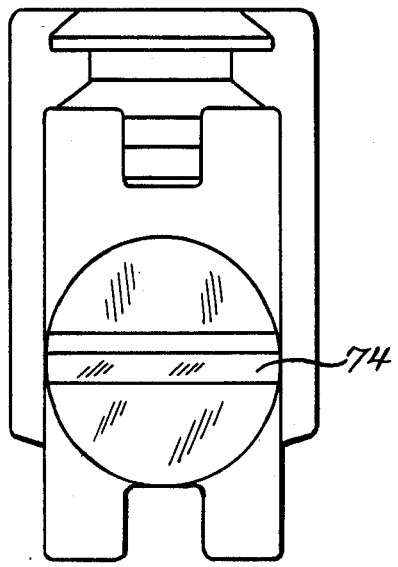
FIG. 17 is a frontal elevational view of the bracket assembly taken from the right side as shown in FIG. 16.

As best seen in FIGS. 11-13, the present invention further includes the bracket insert 16 formed generally in the shape of a cylindrical portion 58, a projection or tang portion 60 and an outer end face portion 62. Cylindrical portion 58 has a longitudinal axis 64 oriented obliquely from the vertical at a slope generally equal to the slope of the axis 46 of bore 14 of the bracket holder 14. Cylindrical portion 58 has formed therethrough a bore 66 oriented substantially horizontal and adaptable to line up and have a longitudinal axis coincident with the coincident axis 50 of transverse bores 48. The diameter of bore 66 is substantially equal to the diameter of bores 48.

Passive fastening means is provided in the form of the pin 18 to fit within bores 48 of the bracket holder 14 and bore 66 of the insert 16 and hold them in assembled relationship in the bracket assembly 10.

The tang portion 60 is shaped to provide an upper horizontal surface 70 and an oblique surface 72. The tang 60 is shaped to interfit with one of the notches 26 of base 12 and be secured thereat by the pin 68 extending through bores 48 of the holder 12 and bore 66 of the insert 56. It should be noted that the tang 60 is depicted as rectangular in end section, but could be of any configuration such as round, and still accomplish the objects of the invention. In addition, the tang 60 could be disposed on the frontal end surface of cylinder 58 in any number of locations around any portion of the circular surface so as to provide a multitude of vertical or rotational adjustments. In this manner, the tang 60 is adaptable to provide tip adjustment by modifying vertical as well as angular adjustments to a tooth.

Figure 18:
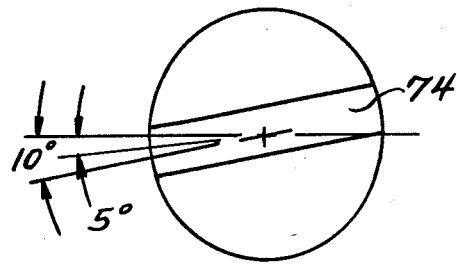
FIG. 18 is a partial outside view of an insert showing its slot with two orientation positions of different degrees on one side of a centerline of the bracket assembly.
Figure 19:
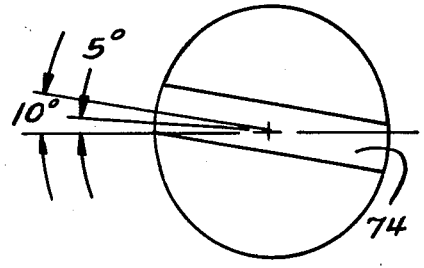
FIG. 19 is a partial outside view of an insert showing its slot with two orientation positions of different degrees on the other side of a centerline of the bracket assembly.

The end face portion 62 of insert 16 slopes outwardly and downwardly for a preselected distance and then changes direction to a vertical orientation that interrupts with a slotted configuration 74. From the bottom of the slotted configuration 74, the end face 62 slopes inwardly and terminates at a bottom spherical configuration of the insert 16. The slot 74 formed in end face 62 is generally horizontal and extends downwardly so as to receive and maintain therein the orthodontic wire (not shown) that is used to establish an arch of normal occlusion. However, it should be understood that an insert 16 could and most probably would be manufactured in a manner that provides any number of desired angular orientations wherein the slot 74 is rotated from a horizontal alignment, such as shown in FIGS. 18 and 19, so as to be adaptable to change and correct a severely malposed tooth into normal occlusion. As will be hereinafter described in greater detail, it is also possible to incline the slot 74 upwardly or downwardly with respect to longitudinal axis 46 (rather than being parallel thereto) so as to create any number of variable forces of torque on a tooth and move it into normal occlusion.

In the operation of the invention, a complete bracket assembly 10, including the base 12, the holder 14, the insert 16 and the pin 18 connecting together the various parts is bonded to each respective tooth to be repositioned in the upper or lower jaw of the mouth. The correct assembly is determined by observing the amount of vertical, tip and torque adjustments required, choosing a base with a desired arcuate surface 20, selecting a specific insert and holder with desired horizontal or angular slot 74, and then bonding the preselected arcuate surface 20 of the base to the malposed tooth. The fastening means 18 is then removed from its position of holding together the assembled parts. It is then possible to retract the insert 16 a slight distance so as to disengage the tang 60 from a slot 26 of the dove-tailed track 24 of the base 12. The holder 14 is then free to slide upwardly or downwardly along the track 24. When it is determined that the vertical position of the holder 14 is disposed upon track 24 in a desired location, the insert 16 is moved upwardly and inwardly so that its projecting tang 60 engages a selected one of the notches 26. The pin 18 is then returned to its position in bores 48 of the holder 14 and bore 66 of the insert 16 to hold together and maintain the assembly in a corrective orientation on the malposed tooth.

Whenever it is determined that further adjustment of the tooth is required, the pin 18 is removed, the insert 16 is retracted to disengage its tang from the notch of the base, the holder is moved upwardly or downwardly on the track 24 to a new position, the insert is then moved into engagement with a newly selected notch of the base, and the pin is again placed in locking arrangement of the assembly. This procedure is repeated as necessary until each tooth is repositioned into a state of normal occlusion. It should be understood that the arch wire is maintained at all times by ligation within a slot 74 of each bracket assembly 10 attached to the teeth of the upper and lower jaw. However, it should be noted that whenever it is desired to make an adjustment of a bracket holder and insert from one position to another on the track of a base member, the ligatures securing the arch wire in a slot 74 are cut, the arch wire is removed, the adjustment is made, the arch wire is returned to the slot and ligatures are again placed in position to maintain the arch wire in slot 74. In this manner the teeth are moved upwardly or downwardly, tipped mesially or distally to a correctly oriented position about the arch wire. Proper torque alignment is achieved by preselecting an appropriate angle of inclination between the slot of the holder and insert with respect to the track of the base member secured to the surface of a tooth. The base member is secured to the tooth in a manner that enables the track of the base member to be oriented in a desired vertical position and ultimately brings about desired tip and vertical adjustment. Selection has then been made of an appropriate bracket holder and insert having a preselected angle of orientation to the base member. The insert engages the track of the base member and the bracket assembly is secured together passively by the pin. It is thus understood that torque forces are created that assist in moving and properly positioning a tooth to achieve an attitude of normal occlusion. This cooperative arrangement differs from the prior art because no frictional lock is required and enables the practioner to achieve all three adjustments of a patient's teeth, including tip, torque and vertical positioning.

When treatment of the patient is complete, of course, the assemblies are removed from the arch wire, the parts are disassembled, and the base is removed from its adherence to the surface of the tooth.

It is possible to reuse in subsequent treatment of a patient all of the component parts of an assembly 10, except for the base member 12.

Now referring to FIGS. 20-28, there is illustrated an alternate embodiment of the present invention. The bracket assembly 10 comprises a reduced number of component parts including a bracket holder 80 as shown in FIGS. 20-22, a base member 82 as shown in FIGS. 23-25 and the parts assembled in three different arrangements as shown in FIGS. 26-28.

The bracket holder 80 comprises a body member 84 formed generally in the shape of a parallelopiped having a substantially vertical slot 86 including an upright transverse surface 88 and two inwardly facing surfaces 90. The holder 80 further includes projecting side members 92 having substantially vertical adjacent surfaces 94 formed at their distal ends. The side members 92 have formed therethrough a plurality of transverse apertures 94, including upper, medial and lower locations. The upper apertures 94 in side members 90 are aligned along a coincident longitudinal axis. Similarly, the medial and lower apertures formed in side members 90 are each aligned along a respective coincident longitudinal axis. Body member 84 has formed at its upper and lower ends a plurality of projections comprising tie wings 96 for receiving ligatures in a manner as described hereinabove.

The bracket assembly 10 includes the base member 82 having at its outer or buccal surface a generally upright, tang or track member 100. A plurality of transverse bores 102 are disposed through the track member 100 at upper, medial and lower locations. The upper, medial and lower bores 102 of track member 100 are aligned along parallel longitudinal axes. The apertures 94 of the bracket holder 80 and the bores 102 of the base member 98 are substantially equal in diameter.

The bracket assembly is fitted together by sliding the slot 86 of a bracket holder 80 over and about the tang 100 of a base member 98 and positioned so that two of the upper, medial or lower apertures of the holder 80 are aligned and coincident with one of the upper, medial or lower bores of the base member 98. A pin 104 is then inserted through the apertures 94 of the holder 80 and the base member bore 102 in alignment therewith. In this manner, the adjacent surfaces 92 of the holder 80 may, but do not necessarily engage against outer curvilinear surfaces 106 of the base member 82. When the base member is bonded to a tooth and an arch wire is secured in slot 108 of the holder 80, there are created force vectors that urge the tooth to be moved upwardly or downwardly, tipped mesially or distally and oriented by torque forces into normal occlusion with respect to the arch wire.

When it is desired to make an adjustment, the practitioner disassembles the holder from the base member by removing the pin, the holder is then moved to have its apertures aligned with one of the other bores of the base member, the pin is reinserted through the holder and the base member, the arch wire is relocated in the slot of the holder and corrective forces continue to be exerted against the tooth.

It should be noted that utilizing the structure herein disclosed, the practioner is enabled to separate vetical from angular adjustments of a malposed tooth. This separation is accomplished similarly to that described with respect to the first embodiment by selecting, interchanging or substituting bracket holders having different slot inclination angles and different associative slot rotational angles to impart a desired movement of a tooth. This choice of a variety of bracket holders makes it possible to correct the position of a malposed tooth without utilizing frictional forces to hold an assembly together that in turn create internal forces in the locking mechanism which cause distortion, fracture or deformation caused by the chewing or mastication of a patient. When these two adjustments can be accomplished separately a much stronger bracket assembly is achieved and avoids creating the aforesaid internal destructive forces within the assembly.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. An adjustable orthodontic bracket assembly comprising
    base member means having an arcuate surface adaptable to be bonded to a buccal surface of a tooth, said base member having disposed on a side opposite from said arcuate surface vertically oriented track means having a plurality of generally horizontally oriented notch means formed therein,
    holding means disposed over and about said track means adaptable to be moved upwardly and downwardly thereon,
    engagement means slidably disposed within said holding means adaptable at times to engage at least one of said plurality of said notch means, and
    fastening means securing together said holding means and said engagement means so as to maintain said engagement means in a locked position with said base member.

2. An adjustable orthodontic bracket assembly as claimed in claim 1 wherein
    said track means of said base means comprises a plurality of cantileverly supported ledge members forming said notches therebetween,
    said notches having an upper generally horizontal surface, a lower generally downwardly extending oblique surface and a vertical surface connected therebetween.

3. An adjustable orthodontic bracket assembly as claimed in claim 2 wherein said holding means comprises vertical slot means slidable upon said track means of said base means, and said engagement means being slidable within said holding means at an angle generally parallel to a slope of the oblique surface of said notches.

4. An adjustable orthodontic bracket assembly as claimed in claim 1 wherein said engagement means has formed therein slotted means for receiving and holding an orthodontic arch wire.

5. An adjustable orthodontic bracket assembly as claimed in claim 4 wherein said slotted means is oriented substantially horizontal.

6. An adjustable orthodontic bracket assembly as claimed in claim 4 wherein said slotted means is oriented at positions of angularity from the horizontal.

7. An adjustable orthodontic bracket assembly as claimed in claim 1 wherein said fastening means comprises a generally horizontally disposed pin, whereby said pin is effective to provide a passive connection that prevents creation of destructive stress factures in said assembly.

8. An adjustable orthodontic bracket assembly comprising base member means adaptable to be bonded to a buccal surface of a tooth, said base member having on one side thereof an arcuate surface for attachment to the tooth, a vertical dove-tailed track disposed on a side opposite from said arcuate surface, said track having formed therein a plurality of notch means, each of said notch means having a generally horizontal surface, an oblique surface and a vertical surface connected therebetween, holder means disposed about said base member for slidable upward and downward movement thereon, said holder means having formed therein vertical slot means formed to be generally complementary to said track of said base member means, having obliquely oriented bore means formed therethrough, and having coincident axes horizontally disposed apertures formed therethrough, said axes of said apertures being transverse to an axis of said obliquely oriented bore means, positive engagement means disposed in slidable engagement within said bore means of said holder means for at times engaging a selected one of said plurality of notches of said base member means, having a generally horizontally disposed bore adaptable to be aligned coincidentally with said apertures of said holder means, having slotted means for receiving and holding an orthodontic arch wire, and passive fastening means adaptable to fit within said apertures of said holder means and said bore of said engagement means for maintaining said engagement means in locked relationship with said base member means.

9. An adjustable orthodontic bracket assembly as claimed in claim 8 wheren said slotted means is oriented in substantially a horizontal position.

10. An adjustable orthodontic bracket assembly as claimed in claim 8 wherein said slotted means is oriented in positions of angularity from the horizontal.

11. The method of correcting the position of a malposed tooth comprising the steps of selecting a base member having an arcuate surface adaptable for bonding to a surface of a tooth, choosing an engagement member having a preselected orientation of a slotted configuration, forming a bracket assembly by joining the base member to the engagement member with fastening means, bonding the base member of the bracket assembly to said tooth, placing an arch wire in said slotted configuration of said engagement member, removing said fastening means, retracting said engagement member from said base member, adjusting the position of engagement between the base member and the engagement member to a preselected vertical position, replacing said fastening means, whereby said bracket assembly is effetive to change and correct the position of said tooth to normal occlusion.

12. An adjustable orthodontic bracket assembly as claimed in claim 4 wherein said slotted means is oriented at preselected positions of inclined angularity with respect to said vertically oriented track means.

13. An adjustable orthodontic bracket assembly comprising base member means having an arcuate surface adaptable to be bonded to a buccal surface of a tooth, vertically oriented track means having a plurality of generally horizontally oriented bores formed therethrough formed on said base member means on a side opposite from said arcuate surface, holding means disposed over and about said track means adaptable to be moved upwardly and downwardly thereon, said holding means having formed therethrough a plurality of generally horizontal pairs of apertures, each said pairs of apertures being aligned along a coincident longitudinal axis, said holding means having formed thereon an outer surface slotted means for receiving and holding an orthodontic arch wire, said holding means being adapted to have at least one of its said pairs of apertures aligned with one of the bores of the base member means, fastening means extending through said one pair of apertures of said holding means and said one bore of said base member means so as to maintain said holding means in a locked position with said base member, whereby said bracket assembly is effective to adjust separately the vertical, angular and torque positions of a tooth.

14. An adjustable orthodontic bracket assembly as claimed in claim 13 wherein said slotted means is oriented substantially horizontal.

15. An adjustable orthodontic bracket assembly as claimed in claim 13 wherein said slotted means is oriented at positions of angularity from the horizontal.

16. An adjustable orthodontic bracket assembly as claimed in claim 13 wherein said slotted means is oriented at preselected positions of inclined angularity with respect to said vertically oriented track means.

* * * * *